United States Patent
Friedberger et al.

(10) Patent No.: US 8,323,953 B2
(45) Date of Patent: Dec. 4, 2012

(54) DETECTION DEVICE FOR DETECTING BIOLOGICAL MICROPARTICLES SUCH AS BACTERIA, VIRUSES, SPORES, POLLEN OR BIOLOGICAL TOXINS, AND DETECTION METHOD

(75) Inventors: Alois Friedberger, Oberpframmern (DE); Ulrich Reidt, Schwalmstadt (DE); Gerhard Müller, Grafing (DE)

(73) Assignee: EADS Deutschland GmbH, Ottobrunn (DE)

( * ) Notice: Subject to any disclaimer, the term of this patent is extended or adjusted under 35 U.S.C. 154(b) by 177 days.

(21) Appl. No.: 12/598,483

(22) PCT Filed: Apr. 29, 2008

(86) PCT No.: PCT/EP2008/055231
§ 371 (c)(1),
(2), (4) Date: Jan. 28, 2010

(87) PCT Pub. No.: WO2008/135452
PCT Pub. Date: Nov. 13, 2008

(65) Prior Publication Data
US 2010/0136556 A1    Jun. 3, 2010

(30) Foreign Application Priority Data
May 4, 2007    (DE) .......................... 10 2007 021 387

(51) Int. Cl.
*C12M 1/00* (2006.01)
*G01N 15/06* (2006.01)
*B01L 3/00* (2006.01)
*B01L 99/00* (2010.01)
*B01D 21/00* (2006.01)

(52) U.S. Cl. ............... 435/283.1; 435/287.1; 435/288.2; 435/288.5; 422/68.1; 422/82.05; 422/82.08; 422/501; 422/527; 422/537

(58) Field of Classification Search .................. None
See application file for complete search history.

(56) References Cited

U.S. PATENT DOCUMENTS

| | | | |
|---|---|---|---|
| 4,915,812 A * | 4/1990 | Parce et al. ................. | 204/403.1 |
| 5,726,026 A | 3/1998 | Wilding et al. | |
| 6,844,157 B2 | 1/2005 | Snaidr | |
| 2004/0063197 A1* | 4/2004 | Tilles et al. ................. | 435/287.2 |
| 2004/0072278 A1* | 4/2004 | Chou et al. ...................... | 435/29 |
| 2004/0203029 A1 | 10/2004 | Snaidr et al. | |
| 2004/0245102 A1* | 12/2004 | Gilbert et al. ................. | 204/451 |
| 2005/0064444 A1 | 3/2005 | Beimfohr et al. | |
| 2005/0136446 A1 | 6/2005 | Snaidr et al. | |
| 2005/0191620 A1* | 9/2005 | McDevitt et al. ................. | 435/5 |
| 2005/0202476 A1 | 9/2005 | Saettler et al. | |
| 2005/0202477 A1 | 9/2005 | Saettler et al. | |
| 2006/0257941 A1 | 11/2006 | McDevitt et al. | |
| 2006/0274309 A1* | 12/2006 | Cerni et al. ................... | 356/338 |
| 2008/0026368 A1 | 1/2008 | Snaidr et al. | |

FOREIGN PATENT DOCUMENTS

DE    103 07 732 A1    8/2004
(Continued)

*Primary Examiner* — Betty Forman
(74) *Attorney, Agent, or Firm* — Global IP Counselors, LLP (57) ABSTRACT

A device for the detection of micro particles that can be marked by probes or antibodies capable of being detected by radiation has a filter, a supply system, and a detection system. Fluid to be examined is passed over a filter to filter out the micro particles and to perform the marking steps by supplying corresponding marking substances to the filter.

19 Claims, 4 Drawing Sheets

FOREIGN PATENT DOCUMENTS

| | | |
|---|---|---|
| DE | 10 2006 026 559 A1 | 12/2007 |
| EP | 1 445 331 A1 | 8/2004 |
| WO | WO-00/65093 A | 11/2000 |
| WO | WO-01/68900 A2 | 9/2001 |
| WO | WO-02/101089 A2 | 12/2002 |
| WO | WO-03/005013 A1 | 1/2003 |
| WO | WO-2004/009840 A1 | 1/2004 |
| WO | WO-2005/031004 A2 | 4/2005 |
| WO | WO-2005/036602 A2 | 4/2005 |
| WO | WO-2005/102528 A1 | 11/2005 |
| WO | WO-2007/024701 A2 | 3/2007 |

\* cited by examiner

DETECTION DEVICE FOR DETECTING BIOLOGICAL MICROPARTICLES SUCH AS BACTERIA, VIRUSES, SPORES, POLLEN OR BIOLOGICAL TOXINS, AND DETECTION METHOD

CROSS-REFERENCE TO RELATED APPLICATIONS

This U.S. National stage application claims priority under 35 U.S.C. §119(a) to German Patent Application No. 10 2007 021 387.7, filed in Germany on May 4, 2007, the entire contents of which are hereby incorporated herein by reference.

BACKGROUND OF THE INVENTION

1. Field of the Invention

The invention relates to a detection device for detecting biological micro particles such as for example living or dead bacteria, viruses, spores, pollen or biological toxins that can be marked using probes capable of being detected by radiation, in particular a detection device for detecting living bacteria, viruses or biological toxins by means of fluorescent nucleic acid probes or proteins as probes. The invention also relates to a detection method for detecting biological micro particles such as for example living bacteria, viruses, spores, pollen and/or biological toxins in a fluid.

2. Background Information

Previous techniques for detecting living bacteria require a time-consuming step of cultivation of the micro organisms. This conventional technique of detection of living cells or cell number determination of living cells requires an enormous amount of time and can be performed only in suitable biological laboratories (S1 to S4 laboratories). An alternative technique for the detection of living bacteria is the in situ hybridization. The in situ hybridization technique is a standard technique already frequently applied in molecular biology. There have been numerous publications on this technique.

Concerning bacteria detection, the company of Vermicon AG, Munich, offers ready-to-use detection kits, i.e. ensembles of chemicals, for different bacterial strain.

Previous detection methods including in situ hybridization are described in more detail in WO 01/68900 A2, WO 02/101089 A2, DE 103 07 732 A1, WO 2005/031004 A2, U.S. Pat. No. 6,844,157B2, US 2005/064444 A1, US/2005/0202477 A1, US 2005/0202476 A1 as well as US 2005/0136446 A1. For further details it is explicitly referred to these prior art documents.

Presently however, the in situ hybridization is possible in the practice only by using a very expensive and highly sensitive fluorescence microscope.

SUMMARY OF THE INVENTION

Accordingly, it is an object of the present invention to provide a method allowing rapid, reliable and uncomplicated automatic detection especially of living bacteria, but also of other micro particles and microorganisms, in particular viruses or biological toxins, that can be marked using special probes.

This object is achieved by a detection device comprising the features of a first aspect of the present invention and by a detection method comprising the steps of a twenty-fourth aspect of the present invention.

Advantageous embodiments of the invention form the subject of other aspects. A beneficial use forms the subject of another aspect.

Advantageous embodiments of the invention enable in particular an automatic live detection of pathogenic bacteria in drinking water and air.

The invention particularly provides a device for rapid and preferably automatic detection of living bacteria, without the aid of a fluorescence microscope.

The measuring results are especially suitable for being used to obtain a correlation to CFU (colony forming units), with the aim of providing an alternative to the approved time-consuming cultivation method (which provides the CFU value).

According to the invention, a filter is provided suitable for filtering out the micro particles to be detected. The substances or chemicals serving in the various marking steps to mark the micro particles for the purpose of detection are provided for instance by a supply system and are also passed to and particularly over the filter. By means of a detection system, the radiation for detecting the probes can be detected and thus also the micro particles.

Especially for the detection of living bacteria a micromechanical filter is used for example. In such a case, a supply system delivers especially the chemicals to be used in the individual steps of an in situ hybridization, for instance from detection kits available on the market for detecting particular bacteria.

The supply system can be preferably automatically controlled via valves and/or pumps, so that the detection method can be performed fully automatically.

Preferably, the filter can be used several times by being regenerated and/or conditioned using suitable chemicals. This is enabled by correspondingly controlled pumps and valves.

In particular, the supply system can be a part of a fluidic system which does not only supply chemicals that are used for marking and/or for the later washing and cleaning of the device, but which is also capable of delivering fluids to be measured to the filter. The measurement of radiation is adapted to the respective probes that are used.

In order for the probes to emit radiation, fluorescent colorants or for instance also Raman labels, quantum dots or the like can be used. If probes marked with a fluorescent colorant are used, as this is known also in the in situ hybridization, a light source for exciting the fluorescent colorant is preferably employed, for example a laser.

As a radiation measuring device for the measurement of radiation correlated to the probes preferably a light detector is used which is sensitive to a particular fluorescence radiation.

The light detector may include for example a photo multiplier, in order to thus detect the intensity of the fluorescent light. Alternatively or additionally a space-resolving light detector, for example a two-dimensional space-resolving light detector can be used. Such a detector is formed for example by a two-dimensional CCD array. Such a space-resolving sensor is capable of determining light pulses and the position of their origin on the filter. Due to the higher resolution and due to the individual sensor elements an evaluation unit, which is preferably controlled by software, can be connected for counting e.g. the light spots and thus the probes and thus the micro particles.

For filtering out living bacteria, a micromechanical filter element can be used for example. Preferably employed are micromechanical filters having a pore size clearly below the size of the micro particles to be filtered out. A micromechanical filter for instance has a pore size of less than 0.8 μm, for example approx 0.45 μm, so that bacteria having typical dimensions of 1 μm are securely retained.

Other interesting micro particles, such as for example viruses or biological toxins, partly have smaller dimensions. For filtering these micro particles, a micromechanical filter having a small pore size or a different filter, particularly a nitrocellulose filter, can be used. For this purpose, a micromechanical filter or a different porous body as a support are covered with nitrocellulose. The nitrocellulose membrane can be provided for instance by a web capable of being moved for the exchange of the effective nitrocellulose membrane, so that a fresh web piece can be used as a filter for new measurements.

For the determination particularly of viruses or biological toxins, proteins detectible by radiation such as antibodies marked with a fluorescent colorant or marked nucleic acid probes can be used.

For the detection of living bacteria, correspondingly marked DNA probes are preferably employed which attach to the mRNA that is only provided by living bacteria having a sufficient lifetime.

Additionally to this probe marking employed in the in situ hybridization also a PCR module can be used to alternatively or additionally perform a PCR detection process.

In the PCR method, which is also employed in criminology, pieces of DNA are multiplied and thereafter detected.

If the concentration of micro particles in liquids is to be determined, for example the number of living bacteria in drinking water, this liquid can be directly supplied to the detection device and passed over the filter. If a concentration of micro particles in gaseous media is to be determined, for example in the air, these micro particles can be first collected in a liquid, for example in an upstream collecting device, e.g. a bio sampler, and this liquid can subsequently be transferred to the detection system, or the particles can be directly collected from the air by passing the air through the filter.

Advantages of the invention and/or advantages of beneficial embodiments of the invention are as follows:

A rapid, uncomplicated and sensitive automatic detection of living bacteria using the detection device is possible at any location.

Time-consuming steps of cultivating bacteria in a biological laboratory can be omitted.

A mobile detection of living cells is possible. This allows for example rapid testing of drinking water in a vehicle or aircraft or spacecraft or, in connection with a robot, for civil and/or military purposes.

The device and the method enable for example rapid examination of suspect liquids, in order to prevent biological attacks, and thus contribute to public safety.

In medicine for example, the device and the method allow a rapid diagnose of bacterial diseases, without examination through the microscope.

BRIEF DESCRIPTION OF THE DRAWINGS

Embodiments of the invention will now be described with reference to the attached drawings, wherein it is shown by.

DETAILED DESCRIPTION OF THE PREFERRED EMBODIMENTS

A method and a device for the detection of micro particles that can be marked by probes capable of being detected by radiation will be more clearly described in the following with reference to the drawings. The device and the method are particularly suited for the detection of living bacteria by means of nucleic acid probes or of viruses or biological toxins by means of proteins including antibodies for the probes. Before explaining the device and the method, the general methods for marking such micro particles by means of such probes will be more clearly explained.

Drinking water contains different living and dead bacteria. A part thereof can be pathogenic. Only the living bacteria are relevant, because these alone multiply and may constitute a health risk.

But many conventional detection methods based upon antibodies or PCR are incapable of differentiating between living and dead bacteria. In the following, a device and a method will be described which in fact allow the detection only of the living and hence the relevant bacteria.

Previous detection methods for detecting living bacteria require a time-consuming step of cultivating micro organisms. For this purpose, the bacterial samples are streaked out on special nutrient media and are incubated (breeded) at a particular temperature for a particular time. Depending on the bacterial species, this cultivation step may continue for several days. After the end of the incubation period, the colony forming unit (CFU), the number of bacteria colonies that have formed, is determined. This conventional technique of living detection or determination of the number of living cells is extremely time-consuming and up to present there is no possibility of a rapid and uncomplicated detection of living bacteria.

An alternative technique for the detection of living bacteria is in situ hybridization. But presently this analyzing method can be carried out only in a very expensive and highly sensitive fluorescence microscope. Mobile field tests are practically impossible and qualified laboratory personnel is required for operating the microscope.

For the detection of microorganisms additional detection methods are frequently applied, for example polymerase chain reaction (PCR) or enzyme-linked immuno sorbent assay (ELISA). But these methods exclusively determine the number of the living and dead cells, hence the total number of cells of a sample. The determination of the number of living cells is not possible with these methods.

2. Methods for Bacteria Detection

A) PCR

The PCR method (polymerase chain reaction) is a method in which smallest amounts of a DNA section can be multiplied in a chain reaction (amplification). Today, the PCR method is frequently used for various proofs by way of particular DNA sequences, for example:

in criminology or in paternity proof in microbiology, for the detection of living and dead bacteria (total cell number)

in medical diagnose, for the proof of virus DNA in the blood, or in evolution biology, for tracing family relations and lines of ancestry.

For PCR detection, two short pieces of DNA (primer) must be present matching the searched DNA strand. The chain reaction initiated by them performs up to 30 cycles, the amount of DNA being doubled at each cycle. Due to the detection via genotype, dead and living bacteria are detected. A detection exclusively of living cells is not possible with the PCR method.

B) ELISA

ELISA (enzyme-linked immuno sorbent assay) is a widespread method of detecting individual proteins (antigen) using the mechanisms of the immune system: If a substance is recognized by the immune system as a foreign substance, the immune system produces antibodies docking to the foreign molecule and thus marking the molecule. This so-called antibody-antigen interaction is utilized for the ELISA test.

If a particular protein has to be detected, the matching antibodies must be known and must have been prepared in advance using various gen-technological or cell-biological methods. If the searched protein is present in a sample, the protein will be bound by the antibodies applied to a substrate. After the antigen-antibody interaction a reaction controlled by enzymes is induced which results in a visible ink precipitate. ELISA tests are very common today in medical diagnose. But they are also used in many other fields, if individual proteins have to be detected. In the case of bacteria detection, the antibody recognizes surface proteins specific to bacteria. Both the living and dead bacteria (total cell number) are detected.

C) In Situ Hybridization

Figure 1:
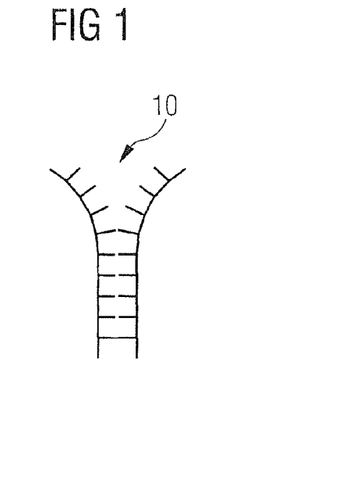
FIG. 1 a DNA sequence for explaining the basics of in situ hybridization.

Reference is made in the following to FIG. 1. A DNA sequence 10 may be imagined as a "zipper". The "teeth" of this zipper are the bases adenine (A), cytosine (C), guanine (G) and thymine (T). The information contained in the DNA is encoded along the "zipper" in the order of these four letters. Opposite "teeth" always only form either AT or GC pairs. The sequence ACGCT for example has the letter sequence TGCGA as a complementary vis-à-vis.

During the hybridization, the "zipper" is opened by heating, so that single strands are exposed. Short pieces of DNA, which are also single-stranded pieces of DNA and which are used as probes, are now supposed to find their matching counterpart on this long single strand. This is the point where the zipper closes again after cooling.

Figure 2:
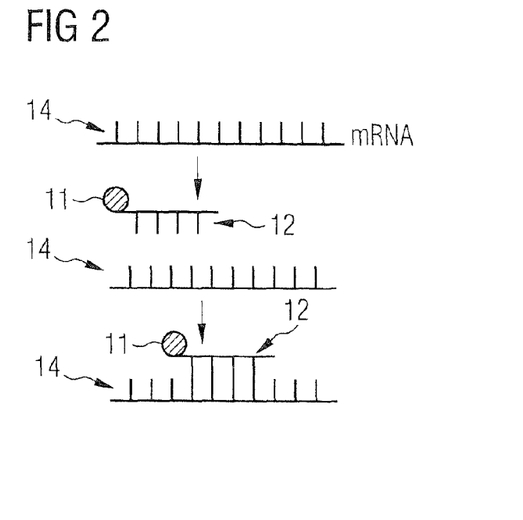
FIG. 2 a schematic illustration of the principle of in situ hybridization.

This can be made visible by means of markings on the probe (e.g. by means of a fluorescent colorant 11, see FIG. 2). In this way it is possible to find out whether or not specific sequences, representing for example particular marker gens, are present in the examined DNA (see item A: PCR).

In the case of in situ hybridization, which is explained in more detail in the following with reference to FIG. 2, the fluorescence-marked probes 12 do not associate with the DNA, but instead with the mRNA 14, the so-called "copy" of the DNA. The mRNA 14 is a kind of copy of the DNA. From the information transcribed into the mRNA, proteins are formed (protein biosynthesis).

In dead bacteria this mRNA 14 has an extremely short lifetime (microseconds) and it is instantly degraded after the dying of the bacteria.

With the in situ hybridization method the mRNA of living cells is preserved (technical expression: "fixed") and then detected, i.e. exclusively the living bacteria are detected (number of living cells), since dead bacteria do no longer contain mRNA.

Since in this method DNA binds to (m)RNA, one speaks of hybridization.

Even a combination of in situ hybridization and PCR is possible. In this case, the DNA of the bacteria which is also fixed is used for amplification. This method, which is called in situ PCR, is employed for instance for the parallel detection of viruses in the sample to be examined.

In the meantime, the in situ hybridization method has developed into a standard method which is already frequently used in molecular biology. For further details concerning the individual steps of the in situ hybridization and of the other detection methods herein presented it is explicitly referred to WO 01/68900, WO 02/101089 A2, DE 103 07 732 A1, WO 2005/031004, U.S. Pat. No. 6,844,157 A1, US 2005/064444 A, US 2005/0202477 A1, US 2005/202476 A1, US 2005/0136446 A1.

Ready-to-use detection kits with ensembles of chemicals are available on the market, e.g. from the company of Vermicon AG, Emmy-Noether-Strasse 2, D-80992 Munich, Germany. However, the detection kits which are currently available on the market require a fluorescence microscope, and the chemicals must be professionally used by qualified personnel.

Figure 3:
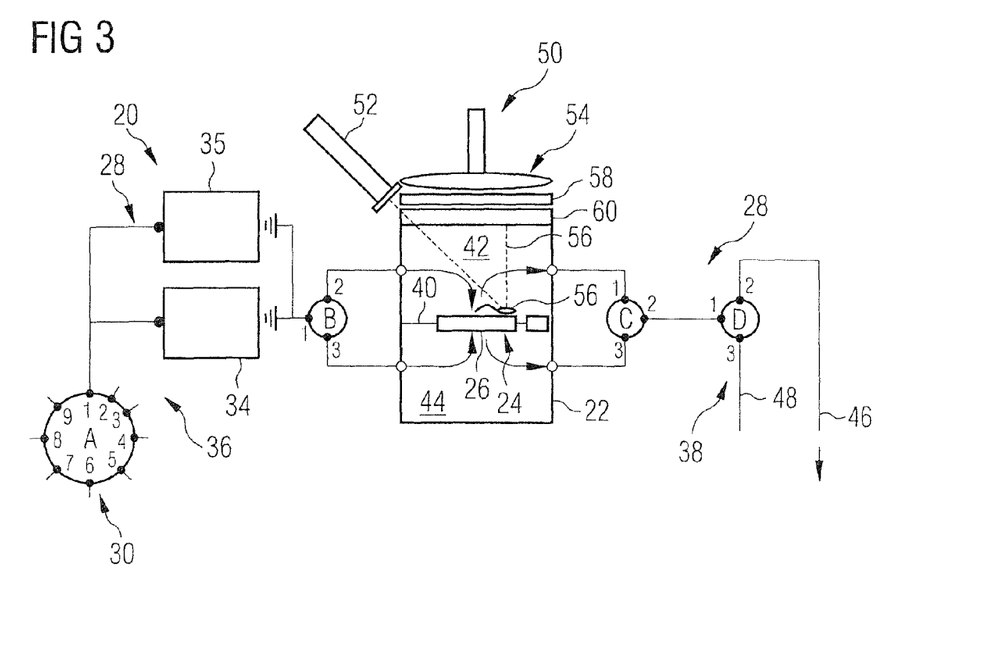
FIG. 3 a schematic illustration of a rapid detection device for detecting living bacteria in drinking water.

Embodiments:

On the other hand, a detection device 20 enabling a fully automated detection of living bacteria without the use of a microscope is illustrated in FIG. 3. The detection device 20 comprises a detection chamber 22 in which a filter 24 is arranged for filtering out the micro particles or microorganisms to be detected from the fluid to be examined.

For the detection of living bacteria the filter 24 is constructed as a micromechanical filter and thus includes a micromechanical filtering element 26. The micromechanical filter and its filtering element for example have a structure which is more clearly described and illustrated in the German patent application DE 10 2006 026 559.9, which is not a prior publication. For further details reference is made explicitly to DE 10 2006 026 559, the contents of which is incorporated herein by reference.

The detection device 20 also includes a fluidic system 28 for passing the fluid, e.g. drinking water, to be examined for the presence of living bacteria 32, to and through the filter 24.

The fluidic system 28 comprises one or more pumps 34, 35 and also several motor valves A, B, C, D. The pumps 34, 35 and the valves A, B, C, D can be automatically controlled by a control unit (not further illustrated) connected to it, e.g. a computer including corresponding software.

Moreover, a part of the fluidic system 28 serves as a supply system 36 adapted for supplying chemicals for marking the bacteria 32 or other microorganisms or micro particles to be detected by means of probes capable of being detected by radiation, for example fluorescence-marked probes 12, to the filter 24. Another part of the fluidic system 28 serves as a discharge system 38 for discharging substances and samples from the detection chamber 22.

More precisely, the supply system 36 of the fluidic system 28 comprises a motor valve A having an outlet A1 and several inlets A2 to A9. The following table 1 shows the configuration of the inlets for a practical example.

TABLE 1

Configuration of the inlets of the motor valve A in a practical example
Valve inlet

| A2 | A3 | A4 | A5 | A6 | A7 | A8 | A9 |
|---|---|---|---|---|---|---|---|
| 20% EtoH | H$_2$O | reserve (inlet is free) | PBS | sample of drinking water | antibody | wash buffer | 0.5 M NaOH |

Two pumps 34 and 35, which are connected in parallel and which have a different pumping capacity, connect to the outlet A1. A first pump 34 works for example in a working range of 6 to 70 ml/min, and a second pump 35 works in a working range of 0.1 to 7 ml/min. Depending on the control and on the switching of the pumps 34, 35, precisely dosed amounts of fluids delivered from the motor valve A can pumped towards the detection chamber 22.

Following the pumps 34, 35 is a 3/2 directional valve B enabling the output of the pumps 34, 35 being selectively directed to one of the two sides of the filter 24. To this end, the detection chamber 22 is subdivided into two sub chambers 42 and 44 by a partition 40, and the sub chambers are interconnected trough the filter 24. While the inlet B1 of the valve B is connected to the outlet of the pumps 34, 35, an outlet B2 of the valve B is connected to the first sub chamber 42, and a second outlet B3 of the valve B is connected to the second sub chamber 44. Depending on whether the first or second sub chambers 42 or 44 are charged, the filter 24 can be charged with corresponding liquids, cleaned and/or conditioned. Corresponding flows can also be achieved via the discharge system 38 in which a first inlet C1 of a 3/2 directional valve C is connected to the first sub chamber 42 and a second inlet C3 is connected to the second sub chamber 44. The 3/2 directional valve C selectively allows the first inlet C1 or the second inlet C3 being switched to an outlet C2. The outlet C2 is connected in turn to an inlet D1 of an additional 3/2 directional valve D. This inlet D1 can be selectively switched by the valve D to a drain 46 for discharging antibodies or to a manifold 48 for collecting antibodies.

That means that by the arrangement of openings for supplying liquid on both sides of the filter and of openings for discharging liquid on both sides of the filter and also by the arrangement of the valves B and C, a flow through the filter 24 in both directions is achieved. By the switchable valve A, which is connected to two or more liquid tanks, chemicals for marking, cleaning or conditioning can flow through the filter.

For the detection of the bacteria 32 marked with the hybridization probes or with fluorescence-marked proteins or antibodies, a radiation measuring device 50 is connected to the detection chamber 22.

To detect for instance bacteria 32 which are marked using fluorescence-marked probes 12, a light source in the form of a laser 52 is required which emits radiation suitable for exciting the fluorescent colorant 11, for example light having a wavelength of 405 nm. This limitation of the wavelength can be further improved by an optical filter connected downstream of the light source.

In the illustrated embodiment the radiation measuring device 50 includes a light detector 54 for detecting the radiation which is used here, namely fluorescence light 56 from the bacteria 32. For a more precise detection of such radiation, the radiation measuring device 50 further includes an optical filtering element 58 which only allows the radiation to be measured, in the present case the fluorescence light 56 to be measured, e.g. fluorescence light at a wavelength 455 nm, to pass through.

For the connection of the radiation measuring device 50, the detection chamber 22 is closed on one side with a quartz glass 60. Excitation by means of the laser 52 and light detection by means of the light detector 54 take place through this quartz glass 60.

Figure 4:
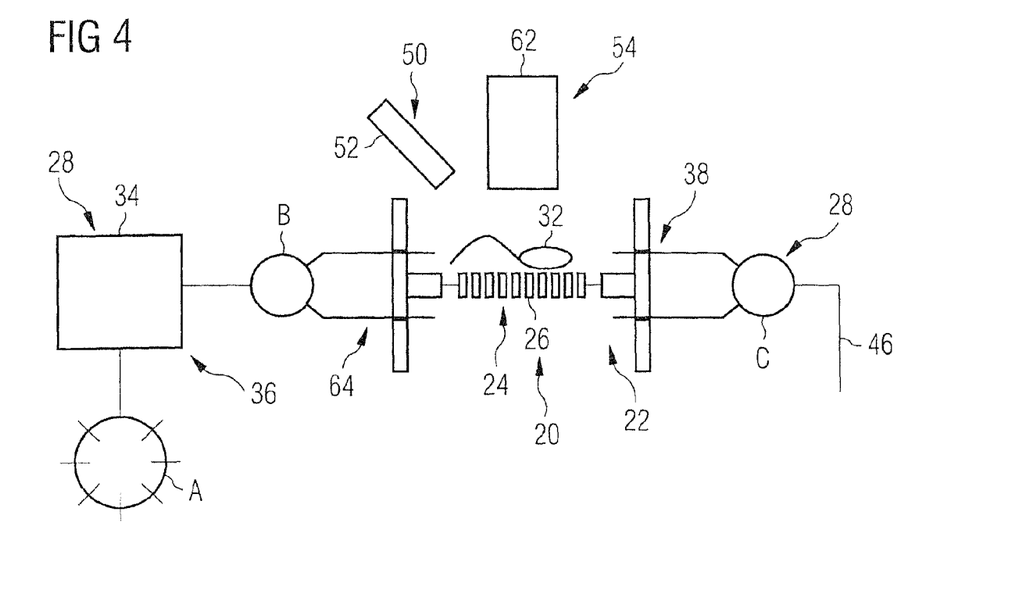
FIG. 4 a schematic illustration of a construction example of a rapid detection device for detecting living bacteria in fluids using a fluidic system with pumps and valves as well as a detection chamber with laser and photo multiplier.

FIG. 4 shows a general drawing of a more special first embodiment of the detection device 20, wherein the detection chamber 22 and the fluidic system 28 are only schematically indicated. In the embodiment illustrated in FIG. 4, the light detector 54 includes a device for measuring the intensity of light, in the present case a photo multiplier 62. In the present case a fluidic system 28 including only a single pump 34 and a simplified discharge system 38 is used.

The detection device 20 shown in the FIGS. 3 and 4 allows a fully automatic detection of living microorganisms using the method of in situ hybridization. Within this system, living bacteria 32 are rapidly and reliably detected for the first time using the in situ hybridization method. The core of the device or of the detection device 20 is the detection chamber 22 containing the micromechanical filter 26. Through the fluidic system 28 (pumps 34, 35, passages or hoses and valves A, B, C, D) connected to the detection chamber 22, the sample to be examined (e.g. water 30 containing bacteria 32) is pumped over the filtering element 26.

Since the micromechanical filtering element 26 has a pore size of e.g. 0.45 µm and since the bacteria 32 have a diameter of e.g. 1 µm, the bacteria 32 will accumulate on the filter surface.

After their accumulation, the bacteria 32 are prepared for the actual detection. To this end, the chemicals required for the in situ hybridization are pumped over the filtering element 26 with the aid of the fluidic system 28, especially with the aid of the supply system 36.

The actual detection is performed using a light source, e.g. the laser 52, which excites the fluorescent colorant 11 with which the DNA probe 12 has been marked. The fluorescence light 56 emitted as a result of the excited fluorescent colorant 11 is subsequently detected by means of the photo multiplier 62 (PMT). Special optical filters—in the present case the optical filtering element 58—ensure that the photo multiplier is reached exclusively by fluorescence light 56 emitted from the marked bacteria 32.

Figure 5:
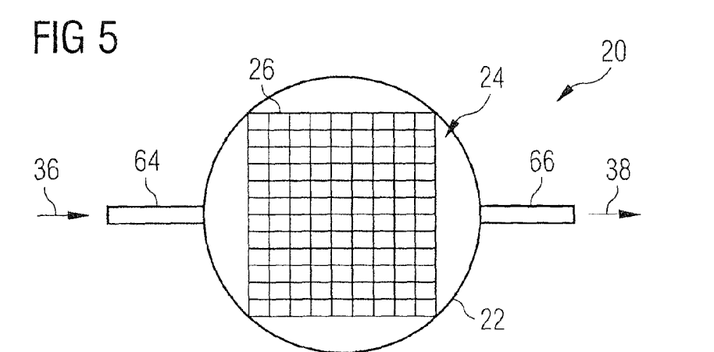
FIG. 5 a schematic drawing of the detection chamber from above, said chamber including a micro mechanical filter.

FIG. 5 is a schematic illustration of the detection chamber 22 including the filter 24 as viewed from above. The grid that can be recognized represents the micromechanical filtering element 20. Also shown are connections 64 and 66 to the supply system 36 respectively the discharge system 38 of the fluidic system 28.

Target organisms for a living detection are for example pathogenic germs. Due to the base sequence of the fluorescence-marked probe 12, it is not only possible to quite specifically detect a pathogenic bacterial species (e.g. E. coli), but it is also possible to detect bacteria on a higher taxonomic level. Hence, in the case of E. Coli, it might be possible that all coli species in a sample are detected.

By designing the base sequence of the DNA probe 12 to be more unspecific, it may become possible to detect on an even higher taxonomic level, e.g. to detect many enterobacteria.

Even a simultaneous detection of different bacterial species is possible. To this end, a mixture of differently marked probes 12 can be employed, using a specific fluorescent colorant 11 for the respective species of bacteria. In this way, it can be determined which bacteria 32 are present in the concentration, if excitation takes place at different wavelengths.

Figure 6:
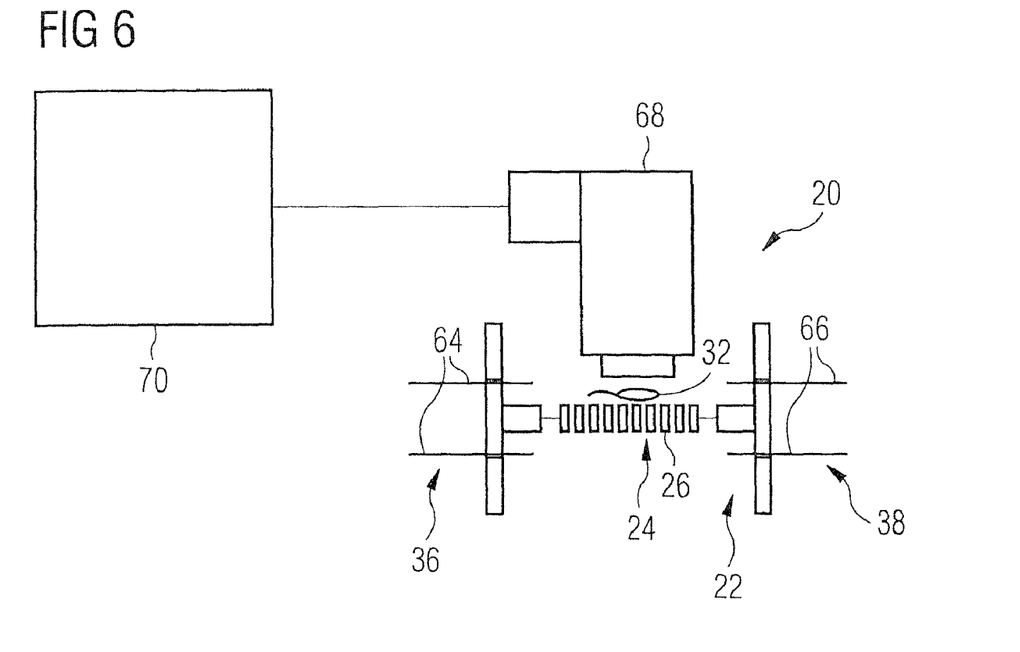
FIG. 6 a schematic illustration of the detection chamber and of a detector of a further embodiment of a detection device.

FIG. 6 schematically shows the detection chamber 22 including the filter 24, and the light detector 54 of a further embodiment of the detection device 20. In this embodiment according to FIG. 6, the light detector 54 does not include a photo multiplier, but a space-resolving detector, namely in the present case a two-dimensional space-resolving detector in the form of a two-dimensional CCD array that is connected to an evaluation unit, for example a computer system 70.

If the detection is not made through a photo multiplier 62, but two-dimensionally by means of a two-dimensional space-resolving detector, e.g. a CCD array 68, plane above the filter 24, the position of the individual bacteria 32 on the filter 24 can be determined. The presentation or resolution on the CCD array can be improved by optics comprised of optical lenses.

By using suitable software, the individual bacteria 32 can be counted. That is, the evaluation unit 70 can count beam pulses or identify the original position of the radiation 56 on the filter 24. This allows the actual number of the bacteria 32 being determined more precisely than by measuring with a photo multiplier 62, because in the latter only the total light intensity is measured.

From the light intensity obtained by the photo multiplier 62 the number of bacteria 32 that had been present is derived through corresponding calibration. Compared thereto, the detection system illustrated in FIG. 6 is capable of immediately outputting the number of bacteria.

The inaccuracy of a measurement through light intensity is the higher the more different is the concentration of mRNA 14 in different bacteria 32.

To detect bacteria in the air or in other gaseous media using the above-described embodiments of the detection device 20, these can be collected for example automatically through a suitable collecting device in a liquid and supplied together with the liquid to the detection device 20, for example through the connection A6. Suitable detection devices are available on the market for example under the name Biosampler from the company of SKC Inc., Eighty Four, Pa., USA.

Alternatively, the air may be directly passed through the filter, in order to accumulate the particles on the filter.

The detection method that can be carried out with the detection device 20 is capable of replacing the current certified cultivation methods for CFU determination. To this end, the probes 12 which are used are so selected that the bacteria 32 detected with these probes are similarly representative as the bacteria detected by the conventional CFU determination.

Figure 7:
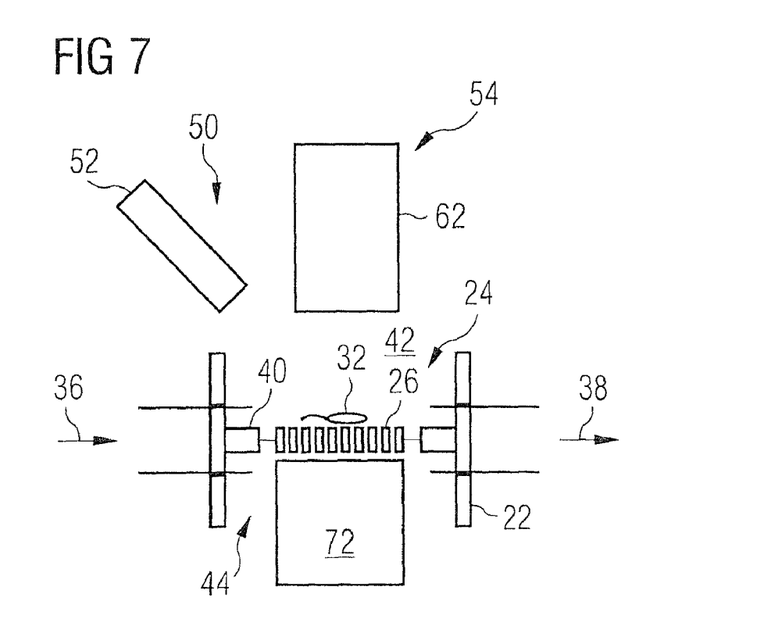
FIG. 7 a schematic illustration of the detection chamber and of detectors of a further embodiment of the detection device in which a combination of in situ hybridization and PCR detection can be performed.

FIG. 7 still shows in a schematic representation the detection chamber 22 including the filter 24 and the radiation measuring device 50 of a further embodiment of the detection device 20.

The embodiment according to FIG. 7 includes an additional module 72—here in the second sub chamber 44—for PCR detection of DNA sequences. The additional module 72 is for example a device for carrying out a real time PCR. Such devices are available on the market, for example from the company of Fluidikm Corp., South San Francisco, USA.

The additional module 72, which is employed in addition to the actual detection device 20, enables a combination of in situ hybridization and PCR. A so-called in situ PCR can be used for example for a subsequent detection of viruses. The actual detection could be made using the method of real time PCR. Thereby, reporter molecules are released during the amplification and due to their fluorescence the reporter molecules can be detected by a photo multiplier.

To this end, the additional module 72 is equipped with a separate radiation measuring device for measuring fluorescence light or it utilizes the correspondingly constructed radiation measuring device 50 of the detection device 20.

The embodiment illustrated in FIG. 7 particularly enables the special embodiment of the detection method more clearly described in the following being carried out. A combination of in situ hybridization and PCR are performed. In the in situ hybridization DNA probes 12 are added after fixing the bacteria 32. The non-bound DNA probes 12 will subsequently be washed away. If the bound DNA probes 12 are now resolved again by the mRNA 14 and amplified by PCR, living bacteria detection can thus be made which even allows detecting extremely small bacteria concentrations.

Hence, the PCR method here not only serves for determining the total number (of dead and living bacteria). On the contrary, the DNA probes previously bound to the mRNA 14, which are only present in living bacteria having a sufficient life time, and multiplied many times by the PCR are detected.

Figure 8:
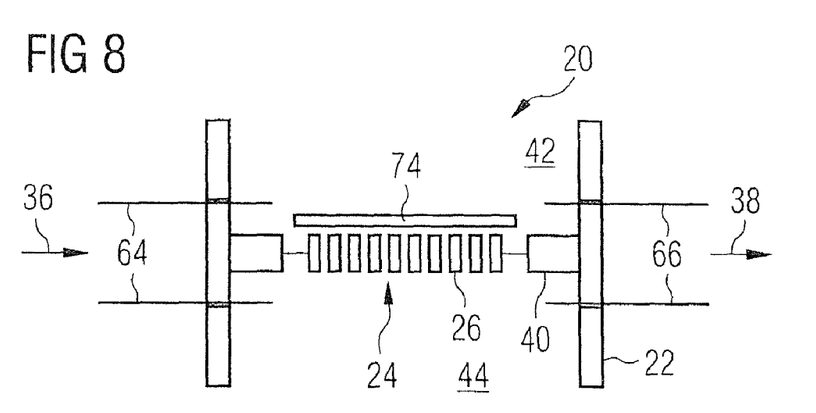
FIG. 8 a schematic illustration of the detection chamber according to a further embodiment.

FIG. 8 shows the detection chamber 22 and the filter 24 of a further embodiment of the detection device 20 which is also capable of automatically detecting viruses and biological toxins. To this end, a membrane, particularly a nitrocellulose membrane 74, is provided. The nitrocellulose layer 74 can be present for example on any permeable body serving as a support. In the embodiment of the detection devices 20 illustrated in the FIGS. 8 and 9 the nitrocellulose membrane 74 is provided as a layer over the micromechanical filtering element 26.

Figure 9:
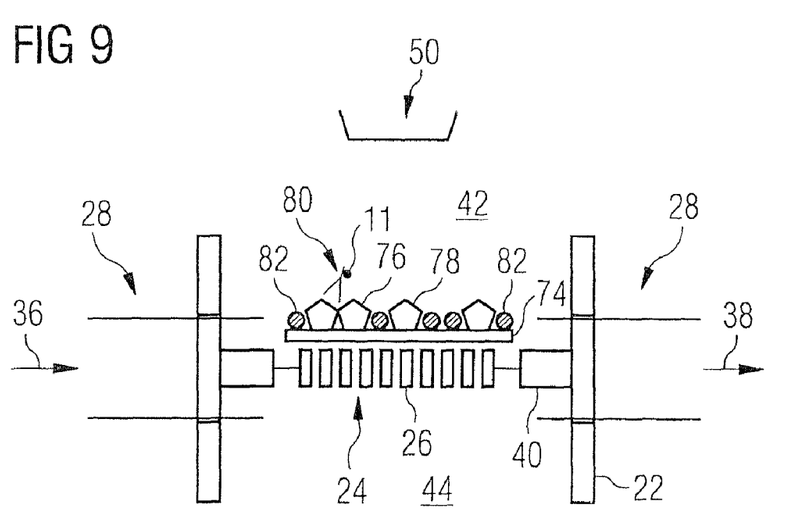
FIG. 9 a schematic illustration for explaining the use of the detection device according to FIG. 8, for detecting viruses and biological toxins.

FIG. 9 illustrates the principle of the filtration of viruses 76 and biological toxins 78 by means of the nitrocellulose as well as the detection by means of fluorescence-marked antibodies as probes which are used for the detection in this detection method.

Accordingly, the FIGS. 8 and 9 more clearly explain a further application of the rapid detection device 20 for the detection of pathogenic viruses 76 and biological toxins 78.

Viruses 76 are small particles (25-500 nm) consisting of a protein shell and—depending on the species of the virus—a RNA or DNA genome. They do not have a metabolism of their own, but propagate exclusively through living cells. Known examples are influenza viruses, ebola viruses or smallpox viruses.

Biological toxins 78 are extremely stable proteins which are mostly formed from bacteria, unicellular organisms or plants as metabolic products.

These toxins are frequently released into the surrounding medium where they become enriched in high concentrations. In the military field biological toxins can be used as biological weapons.

Known representatives of biological toxins are botulinum-toxin (botox) and ricin that can be obtained from the seeds of the castor plant.

Due to their small size, viruses 76 and biological toxins 78 can accumulate only to a limited extent on micromechanical filters. By covering the micromechanical filtering element 26 or a different permeable body, which serves as a support, with a suitable absorbing material, especially nitrocellulose 74, viruses 76 and biological toxins 78 may nevertheless be successfully filtered.

Nitrocellulose exhibits great affinity towards proteins and nucleic acids. Due to their surface condition, proteins are irreversibly bound to the nitrocellulose membrane 74. In this way, whole viruses with their surface proteins can be fixedly bound to the nitrocellulose membrane 74.

Binding proteins and whole viruses to nitrocellulose is a widely spread method in the field of biological research and is described in numerous publications ("Westernblot" or "Dot-blot").

After the viruses 76 have become adhered to the diaphragm 74, the positions of the membrane which are still unoccupied can be filled up with particular proteins (e.g. BSA bovine serum albumin) 82. This process is called blocking the membrane. After the blocking the actual detection with specific antibodies 80, which have been marked with fluorescent colorant 11, takes place.

Due to this special property of the nitrocellulose it is possible to suck the sample and all the liquids required for detection through the membrane 74.

Should sucking through the membrane 74 be restricted for some reasons or even be impossible, the membrane 74 could also be superficially washed using the detection device. This would merely require a different switching sequence of the 3/2 directional valves B, C which are positioned next to the detection chamber 22 on the left and right sides thereof (FIG. 4).

All steps of all of the above-described detection methods can be carried out fully automatically with the present device—the detection device 20—that has been developed, so that analyses are possible also without specially trained personnel.

Other than for the examination of liquids a device equipped with nitrocellulose could also be used for the examination of air. If viruses 76 or toxins 78 present in air shall be detected, the same automatic program as for liquids can be used, with air or any other gaseous medium being pumped through the filter.

For making numerous measurements one after the other, the membrane 74 can be provided in the form of an endless roll of nitrocellulose, a unit of which is paid off after each measurement, thus ensuring that the filter 24 is fresh prior to each measurement.

What is claimed is:

1. A detection device to detect biological micro particles, comprising:
    a filter disposed between a first sub chamber and a second sub chamber in a detection chamber, the filter being configured to filter out micro particles to be detected from a fluid to be measured;
    a supply system including a first inlet conduit fluidically coupled to the first sub chamber and a second inlet conduit fluidically coupled to the second sub chamber, a first valve configured to selectively connect one of a plurality of sources of chemicals to an outlet connection to supply to the outlet connection at least one respective chemical from the one of the sources, first and second pumps, each with a different pumping capacity, connected to the outlet connection and configured to provide the respective chemical to a valve inlet, and a second valve configured to selectively provide the respective chemical from the valve inlet to one of the first and second sub chambers via one of the first and second inlet conduits to mark the micro particles to be detected with probes, the probes being radiation emitting nucleic acid probes or radiation emitting proteins, and the supply system being further configured to operate the first valve, the first and second pumps, and the second valve to selectively supply at least one other of the chemicals from at least one of the plurality of sources to one of the first and second sub chambers via one of the first and second inlet conduits to regenerate the filter and to supply cleaning agents or conditioning agents through or to the filter;
    a discharge system including a first outlet conduit fluidically coupled to the first sub chamber and a second outlet conduit fluidically coupled to the second sub chamber, the discharge system being configured to selectively fluidically couple one of the first and second sub chambers to a discharge outlet via one of the first and second outlet conduits based on the one of the first and second sub chambers to which the supply system is supplying the respective chemical; and
    a detection system being configured to detect the probes through the detection of radiation emitted by the probes.

2. The detection device according to claim 1, wherein at least one of the first and second valves includes a motor valve.

3. The detection device according to claim 1, wherein the supply system is a part of a fluidic system that is configured to supply the fluid to be measured to the filter.

4. The detection device according to claim 1, wherein the detection system includes a radiation measuring device to measure the radiation emitted from the probes and an evaluation unit that determines the concentration and/or the number of the micro particles on the basis of the measurement by the radiation measuring device.

5. The detection device according to claim 4, wherein the radiation measuring device includes a two-dimensional space-resolving detector that is configured to detect the radiation and its original position on the filter.

6. The detection device according to claim 4, wherein the evaluation unit is constructed and adapted to count beam pulses or identify the original position.

7. The detection device according to claim 1, wherein the detection system includes a light source to excite fluorescent probes and a light detector to detect light radiation emitted from excited fluorescent probes.

8. The detection device according to claim 7, wherein the light source includes a laser or an LED.

9. The detection device according to claim 7, wherein the light detector includes a photo multiplier and/or a two-dimensional CCD array.

10. The detection device according to claim 9, wherein the detection system includes a radiation measuring device to measure the radiation emitted from the probes and an evaluation unit that determines the concentration and/or the number of the micro particles on the basis of the measurement by the radiation measuring device, and the evaluation unit determines the concentration of the micro particles from the light intensity measured by the photo multiplier.

11. The detection device according to claim 7, further comprising
    at least one optical filtering element that exclusively allows the fluorescence light emitted from the probes to pass through to the light detector.

12. The detection device according to claim 1, further comprising
    a control that controls the detection device.

13. The detection device according to claim 1, wherein the supply system is controlled to supply DNA probes as the probes in the chemicals such that the DNA probes become respectively attached to the mRNA of the living bacteria present at the filter to mark the living bacteria by in situ hybridization.

14. The detection device according to claim 13, wherein the one of the plurality of sources includes a source that delivers the DNA probes configured to be detected by radiation and designed, due a base sequence, such that they match with several bacterial species of a bacterial group.

15. The detection device according to claim 1, wherein the supply system is adapted for delivery of differently marked probes for simultaneous detection of different micro particles.

16. The detection device according to claim 1, further comprising
a collecting system, in which micro particles from a gaseous medium to be measured are collected in a liquid and discharge liquid of the collecting system is configured to be passed via the filter.

17. The detection device according to claim 1, further comprising
an additional module with which a PCR detection of micro particles is configured to be performed.

18. The detection device according to claim 1, wherein
the filter includes a micromechanical filtering element that attracts micro particles, and/or a nitrocellulose membrane that attracts micro particles.

19. The detection device according to claim 18, wherein
the nitrocellulose membrane has a web of nitrocellulose configured to be wound forward between measurements.

\* \* \* \* \*